United States Patent [19]

Okawa et al.

[11] Patent Number: 5,502,244
[45] Date of Patent: Mar. 26, 1996

[54] PROCESS FOR PRODUCING ISOCYANATES

[75] Inventors: Takashi Okawa; Toshinari Aoki; Hiroshi Matsunaga; Hideo Igarashi, all of Niigata, Japan

[73] Assignee: Mitsubishi Gas Chemical Company, Inc., Tokyo, Japan

[21] Appl. No.: 405,014

[22] Filed: Mar. 16, 1995

[30] Foreign Application Priority Data

Mar. 18, 1994 [JP] Japan .................................. 6-048690

[51] Int. Cl.⁶ .............................................. C07C 263/00
[52] U.S. Cl. ............................................................ 560/345
[58] Field of Search ............................................. 560/345

[56] References Cited

U.S. PATENT DOCUMENTS

| | | | |
|---|---|---|---|
| 4,081,472 | 3/1978 | Tsumura et al. | 260/453 |
| 4,388,246 | 6/1983 | Sundermann et al. | 260/453 |
| 5,087,739 | 2/1992 | Bohmholdt et al. | |

FOREIGN PATENT DOCUMENTS

| | | |
|---|---|---|
| 2015223 | 11/1990 | Canada . |
| 0355443 | 2/1990 | European Pat. Off. . |
| 0396976 | 11/1990 | European Pat. Off. . |
| 54-88201 | 7/1979 | Japan . |
| 57-158747 | 9/1982 | Japan . |

OTHER PUBLICATIONS

Synthetic High Polymers–Fred W. Billmeyer–Chemical Abstracts, vol. 91, No. 2, Jul. 9, 1979.

*Primary Examiner*—José G. Dees
*Assistant Examiner*—Samuel Barts
*Attorney, Agent, or Firm*—Armstrong, Westerman, Hattori, McLeland & Naughton

[57] ABSTRACT

Provided is a process for producing isocyanates from carbamic acid esters which comprises thermally decomposing carbamic acid esters in the presence of a catalyst containing at least one compound selected from the group consisting of organic sulfonic acids and alkaline metal salts of organic sulfonic acids. Thereby, a high thermal decomposition rate can be provided and isocyanate can be obtained in a high yield.

4 Claims, No Drawings

PROCESS FOR PRODUCING ISOCYANATES

BACKGROUND OF THE INVENTION

1. Field of the Invention

The present invention relates to a process for producing isocyanates by thermal decomposition of carbamic acid esters. Isocyanates are useful as raw materials for producing polyurethane, polyurea, etc., and have been commercially produced on a large scale.

2. Prior Art

Isocyanates have been industrially produced, usually by the reaction of amines with phosgene, i.e., the so-called phosgene process. However, the phosgene process has problems in handling of phosgene having intensive toxicity, treatment of hydrochloric acid being by-produced in a large amount, corrosion for apparatuses, etc., and thus, instead of the phosgene process, development of an industrially distinguished process for production of isocyanates has been keenly desired.

As one process thereof, there is a process for thermally decomposing carbamic acid esters. It is known that isocyanates can be obtained by heating carbamic acid esters in a liquid phase. However, in the absence of a catalyst, a thermal decomposition rate is generally low, and when a thermal decomposition temperature is elevated, high boiling point by-products increase, so that a yield tends to decrease. Accordingly, as processes for ensuring a high thermal decomposition rate and suppressing side reactions, various processes for using a catalyst, a stabilizer, etc., have been proposed.

That is, a process for producing isocyanates by thermal decomposition of carbamic acid esters in the presence of a catalyst, for example, includes a process for using a catalyst dissolved in a solvent at least one metal thereof selected from the group consisting of metallic atoms belonging to IB, IIB, IIIA, IVA, IVB, VB and VIII groups in the periodic table of elements or a metallic compound thereof, as disclosed in U.S. Pat. No. 4,081,472. JP-A-54-88201 discloses a process for using an alkaline earth metal(s) and a metallic compound(s) thereof as a catalyst. JP-A-57-158747 discloses a process for using at least one of elements or compound selected from elements belonging to copper group, zinc group, aluminium group, carbon group except carbon, and titanium group in the periodic table of elements and oxides or sulfides thereof in a solvent as a heterogeneous catalyst.

U.S. Pat. No. 4,388,246, in order to suppress side reaction in which high boiling point by-products are produced, proposes a process for using a stabilizer selected from the group consisting of hydrogen chloride, organic acid chloride, substances having an alkylation function being composed of an alkyl ester of organic or inorganic acid and organic tin-(VI)-chloride in the presence or absence of the above-mentioned catalyst.

A process for producing isocyanates by thermal decomposition of carbamic acid esters (urethanes), even in case of using the above-mentioned catalyst or stabilizer, suffers from such disadvantages as much formation of high boiling point by-products or a low space-time yield.

Accordingly, it has been proposed to use a homogeneous or heterogeneous catalyst being composed a heavy metal(s) including Co, Mn, Fe, Ni, etc., or a metallic compounds(s) thereof. However, in such catalysts, a catalyst composition deposits along with high boiling point by-products with catalyst's deterioration or deactivation, etc., to cause adhesion or sedimentation on the inside of a reactor, so that it becomes difficult to ensure a long-term stationary operation. Further, these catalysts after use are separated along with high boiling point by-products from a solvent in an evaporator, a filter, etc. A treatment for the separated by-products is complicated because a heavy metal(s) is contained in the by-products.

The object of the present invention is to provide a process for producing isocyanates by thermal decomposition of carbamic acid esters in which a high thermal decomposition rate is ensured and side reaction wherein high boiling point products are produced is suppressed and furthermore isocyanates can be stationarily produced in a high space-time yield for a long term.

SUMMARY OF THE INVENTION

As a result of extensive studies to solve the problems encountered in the use of a catalyst for thermal decomposition of carbamic acid esters and in the production of isocyanates by thermal decomposition of carbamic acid esters, the present inventors have found that a high thermal decomposition rate can be provided and an amount of high boiling point by-products is small and isocyanates can be obtained in a high yield, by using organic sulfonic acids or alkaline metallic salts of organic sulfonic acids as a catalyst and further that stationary operation can be carried out and a treatment for catalyst after use becomes easy, and has established the present invention.

That is, the present invention provides a process for producing isocyanates from carbamic acid esters which comprises thermally decomposing carbamic acid esters at a temperature of 150° to 350° C. in the presence of a catalyst containing at least one compound selected from the group consisting of organic sulfonic acids and alkaline metal salts of organic sulfonic acids and alkaline metal salts of organic sulfonic acids and then separately recovering the resulting isocyanates and alcohols.

DETAILED DESCRIPTION OF THE INVENTION

The present invention will be described in detail below.

The catalyst for use in the present invention is selected from organic sulfonic acids and alkaline metal salts of organic sulfonic acids.

The organic sulfonic acids are compounds being represented by the following general formula (I):

$$R^1SO_3H \qquad (I)$$

wherein $R^1$ is an organic group selected from the group consisting of aliphatic groups, alicyclic groups, aromatic groups and aralkyl groups. $R^1$ may further contain substituted groups non-reactive to isocyanates in the organic group, e.g., halogen groups, alkoxy groups, nitro groups, etc.

Examples of the organic sulfonic acids include aliphatic sulfonic acids including methanesulfonic acid, ethanesulfonic acid, propanesulfonic acid, isopropanesulfonic acid, butanesulfonic acid, pentanesulfonic acid, hexanesulionic acid, heptanesulfonic acid, octanesulfonic acid, nonanesulfonic acid, decanesulfonic acid; aromatic sulfonic acids including benzenesulfonic acids, ortho-, meta- and para-toluenesulfonic acids, metaxylene-4-sulfonic acid, orthoxylene-4-sulfonic acid, metachlorbenzenesulionic acid, parachlorbenzenesulfonic acid, 2,4-dichlorbenzenesulfonic acid, parabromobenzenesulfonic acid, naphthalene-α-sulfonic acid, naphthalene-β-sulfonic acid, etc.

The alkaline metal salts of organic sulfonic acids are compounds being represented by the following general formula (II):

$$R^1SO_3M \qquad (II)$$

wherein $R^1$ is the same as in the general formula (I); and M is an alkaline metal including Li, Na, K, Cs, etc., e.g., sodium salts, potassium salts of the above-mentioned organic sulfonic acids, etc.

The catalyst for use in the present invention may be a mixture of two or above compounds selected from the above-mentioned compounds.

The amount for use of the catalyst is in the range of 0.0001 to 10% by weight to a reaction solution, preferably in the range of 0.001 to 1% by weight.

The carbamic acid esters being as a raw material in the process for producing isocyanates according to the present invention are compounds being represented by the following general formula (III):

$$R^2(NHCOOR^3)_n \qquad (III)$$

wherein $R^2$ and $R^3$ are the same or different from each other and each is an organic group selected from the group consisting of saturated or unsaturated aliphatic groups, alicyclic groups, aromatic groups and aralkyl groups, and n is an integer of 1 to 4.

Aliphatic groups in $R^2$ and $R^3$ for example includes alkyl groups including methyl, ethyl, propyl, isopropyl, butyl, isobutyl, amyl, isoamyl, hexyl, heptyl, octyl, nonyl, decyl, dodecyl, octadecyl, etc.; alkylene groups including ethylene, propylene, butylene, amylene, hexylene, octylene, etc.; alkenyl groups including propenyl, butenyl, pentenyl, etc.

Alicyclic groups in $R^2$ and $R^3$, for example, include cyclopentyl, cyclohexyl, cycloheptyl, cyclooctyl, etc.

Aromatic groups and aralkyl groups in $R^2$ and $R^3$, for example, include phenyl, tolyl, xylyl, naphtyl, biphenyl, anthnyl, etc.

These organic groups may further contain substituted groups non-reactive to isocyanates in the organic group, e.g., halogen groups, alkoxy groups, nitro groups, etc.

Examples of the carbamic acid esters for use in the present invention include aliphatic carbamic acid esters including 1,4-bis (methoxycarbonylamino) butane, 1,6-bis (methoxycarbonylamino) hexane, 1,8-bis (methoxycarbonylamino) octane, etc.; alicyclic carbamic acid esters including 1,3- or 1,4-bis (methoxycarbonylamino) cyclohexane, 1,3- or 1,4-bis (methoxylcarbonylaminomethyl) cyclohexane, 3-methoxycarbonylaminomethyl-3,5,5 -trimethyl-1-methoxylcarbonylaminocyclohexane, bis (4-methoxycarbonylaminocyclohexyl) methane, 1-methyl-2,4-bis (methoxycarbonylamino) cyclohexane, etc.; aromatic carbamic acid esters including 1,3- or 1,4-bis (methoxycarbonylamlnomethyl) benzenes, 1,3- or 1,4-bis (methoxycarbonylamino) benzene, 1-methyl-2,4-bis (methoxycarbonylamino) benzene, 1-methyl-2,6-bis (methoxycarbonylamlno) benzene, 2,4'- or 4,4'-bis (methoxycarbonylamino) diphenyl methane, 4,4'-bis (methoxycarbonylamino) biphenyl, 1,5- or 2,6-bis (methoxycarbonylamino) naphthalene, 1,5- or 2,6-bis (methoxycarbonylamlnomethyl) naphthalene, etc.; carbamic acid esters having ethoxycarbonylamino-substituted group or phenoxycarbonylamino-substituted group in place of methoxycarbonylamino-substituted group in each compounds, etc. These carbamic acid esters can be used alone or in a mixture of two or above members.

The solvent inert to isocyanates also can be used in the present invention. The solvent includes aliphatic, alicyclic and aromatic, substituted or non-substituted hydrocarbons, esters, ketones, ethers, etc. Examples of the solvent include alkanes including hexane, heptane, nonane, decane, etc.; aromatic hydrocarbons including benzene, toluene, xylene, biphenyl, naphthalene, benzyltoluene, pyrene, triphenylmethane phenylnaphthalene, benzylnaphthalene, etc.; esters including dibutyl phthalate, dioctyl phthalate, didecyl phthalate, etc.; ketones including methylethylketone, acetophenone, etc.; ethers including anisole, diphenylether, etc.

The amount for use of the solvent is in the range of 0.05 to 20 times by weight to a carbamic acid ester, preferably in the range of 0.1 to 10 times by weight.

The reaction temperature for thermal decomposition of carbamic acid esters is in the range of 150° to 350°C., preferably in the range of 200° to 300° C. When the reaction temperature is below 150° C., the thermal decomposition rate will be lower, whereas above 350° C. it is unpreferable because side reactions will increase.

It is possible to conduct the reaction usually under a reduced pressure, if necessary, under an atmospheric pressure or an applied pressure.

The reaction time depends on species and amount of catalyst being used, reaction temperature, reaction pressure, reaction system, etc., and is usually in the range of 0.2 to 5 hours.

In the process according to the present invention, carbamic acid esters are thermally decomposed to convert into corresponding isocyanates and alcohols. In order to prevent both from again binding and reverting to original carbamic acid esters, it is necessary to separately recover isocyanates and alcohols. As a process thereof, there is a process for separating and removing by distillation, etc., only a low boiling point component(s) among components being produced with the progress of reaction. In order to promote the separation, an inert gas such as nitrogen, argon, methane, etc., or a low boiling point and inert organic solvent., e.g., benzene, hexane, etc., can be employed in the reaction. Further, there is also another process for withdrawing by distillation etc., both vapors of isocyanates and alcohols being produced with the progress of reaction outside the reaction system and partially condensing the vapors based on the difference condensation temperature to separately recover.

The operation for thermal decomposition carbamic acid esters can be carried out batchwise. Practically, a flow type using a perfectly mixing type of reactor or a tubular type of reactor is preferable. In a flow type, the operation can be suitably carried out by continuously feeding a raw solution being composed of a carbamic acid ester, a solvent and a catalyst in a reactor for thermal decomposition maintained under a reduced pressure, for example, using a multistage type of distillation column as the reactor for thermal decomposition, and then partially condensing both vapors of isocyanates and alcohols being produced in reaction outside the reaction system. The isocyanate distillate thus obtained, if necessary, is purified by distillation, etc., to obtain a high purity of product. On the other hand, the holdup solution from the reactor is continuously or intermittently withdrawn to remove high boiling point by-products with a vaporizer, etc., and solvent, etc., are recycled to a raw material zone.

The organic sulfonic acids or alkaline metal salts of organic sulfonic acids in the non-heavy metallic catalyst according to the present invention promote thermal decomposition of carbamic acid esters and suppress side reactions from isocyanates being produced, whereby isocyanates can be produced in a high space-time yield. Stationary operation for reactor can be carried out for a long term, by using the present catalyst because the catalyst component fails to deposit along with high boiling point by-products. Further, a catalyst after use is separated from a solvent along with high boiling point by-products in a vaporizer, a filter, etc. The separated catalyst can be easily treated because no heavy metals are contained.

PREFERRED EMBODIMENTS OF THE INVENTION

The present invention will be described in detail below, referring to Examples, which are not limitative of the present invention.

EXAMPLE 1

A thermal decomposition rate for 1,3-bis (methoxycarbonylaminomethyl) cyclohexane (which will be hereinafter referred to as "1,3-BUC") was determined on a reaction distillation method. A thermal decomposition rate in the absence of a catalyst also was determined.

A four-necked flask having a capacity of 300 ml, provided with a capillary, a thermometer, a nozzle for sampling of reaction solution and a head for fractional distillation fitted with a reflux condenser, was used as a reactor. The head for fractional distillation of 1,3-bis (isocyanatemethyl) cyclohexane (which will be referred as to "1,3-BIC"), and warm water at 60° C. was circulated through the reflux condenser. The upper portion in the reflux condenser was connected to a vacuum line through a trap for collection of methanol cooled with dry ice. The nozzle for sampling a reaction solution was connected to another vacuum line via a receiver. 15 g of 1,3-BUC, 150 g of Marotherm S (main component; benziltoluene, made by Hüls Co. ) solvent and 0.15 g of naphthalene-β-sulfonic acid as a catalyst was charged into the reactor and replacement was made with nitrogen, and then the interior of the reactor was maintained to 30 mmHg. Then, the reactor was placed in an oil bath kept its temperature at 265° C. The experiment for thermal decomposition was carried out to start the reaction when a liquid temperature reached to 260° C. After the reaction starting, sampling for the reaction solution was conducted every designated time, and components thereof were analyzed by gas-chromatgraphy to investigate change in 1,3-BUC concentration.

On the assumption that the thermal decomposition of carbamic acid ester is a first-order reaction for carbamic acid ester concentration, the thermal decomposition rate was determined. As a result, it was found that thermal decomposition rate $k_1$ was equal to 1.91 $h^{-1}$.

COMPARATIVE EXAMPLE 1

The experiment for thermal decomposition of 1,3-BUC was carried out in the absence of a catalyst in the same manner as in Example 1 and the thermal decomposition rate was determined. As a result, it was found that thermal decomposition rate $k_1$ was equal to 0.145 $h^{-1}$. Thereby, it was found that the thermal decomposition rate in Example 1 increased more by 13 times than that in the absence of a catalyst.

EXAMPLES 2 to 8

The experiments for thermal decomposition of 1,3-BUC were carried out using 0.15 to 0.29 g of methanesulfonic acid, benzenesulfonic acid, paratoluenesulfonic acid, metaxylene-4-sulfonic acid, potassium methanesulfonate or sodium metaxylene-4sulfonate, respectively and the decomposition rates were determined.

The experimental results including the results in Comparative Example 1 and Example 1 are shown in table 1.

EXAMPLE 9

A five-necked flask having a capacity of 500 ml, provided with a capillary, a thermometer, a nozzle for feeding of raw material, a nozzle for withdrawal reaction solution and a packed column (Dixon packing; about eight stages) fitted with a head for fractional distillation was used as a reactor. 350 ml of a solution dissolved 50 ppm of paratoluenesulfonic acid in Marotherm S solvent was charged into the flask, and the flask was placed on the inside of a mantle heater. The head for fractional distillation was fitted with a receiver for collection of 1,3-BIC and a reflux condenser and warm water at 60° C. was circulated through the reflux condenser. The upper portion in the reflux condenser was connected to a vacuum line through a trap for collection of methanol cooled with dry ice. The nozzle for withdrawal of reaction solution was connected to a control valve and then another vacuum line through a receiver.

1,3-BUC / Marotherm S was charged in a ratio ½ by weight into a bath for raw material maintained at a constant temperature and then paratoluenesulfonic acid was added thereto to prepare a solution having paratoluenesulfonic acid concentration of 50 ppm. The raw material solution was fed from a nozzle into the reactor at a flow rate of 150 g/h, using a fixed quantity pump, while keeping the solution temperature in the reactor at 250° C. and the pressure in the interior of the reactor to 22 mmHg. 1,3-BIC and methanol produced by the reaction each was collected in the receiver. Holdup liquid in the reactor was continuously withdrawn so as to maintain the liquid level to a constant level. After the reaction starting, a liquid quantity in each receiver was determined every designated time, and components thereof were anaylzed by gaschromatgraphy. Data in a stationary state were analyzed. As a result, it was found that the selectivity to 1,3-BIC was 96.8% and the selectivity to monoisocyanate as an intermediate product was 1.6% in the 1,3-BUC decomposition percentage of 99.6%. The operation was continued for 12 hours. Neither adhesion nor sedimentation of solid substances was observed in both the reactor and the receiver.

EXAMPLE 10

The experiment of thermal decomposition of 1,3-bis (methoxycarbonylaminomethyl) benzene (which will be referred as to "MXDU") was carried out in the same manner as in Example 9 except that naphthalene-β-sulfonic acid was used as a catalyst species and an amount for use of catalyst was 20 ppm as a solution concentration.

After the reaction starting, a liquid quantity in each receiver was determined every designated time, and components thereof were analyzed by both liquidchromatgraphy and gaschromatgraphy. Data in a stationary state were analyzed. As a result, it was found that the selectivity to methaxylylene diisocyanate was 95.8% and the selectivity to monoisocyanate as an intermediate product was 2.7% in the MXDU decomposition percentage of 99.4%. The operation was continued for 12 hours. Neither adhesion nor sedimentation of solid substances was observed in both the reactor and the receiver.

COMPARATIVE EXAMPLE 2

The experiment for thermal decomposition of MXDU was carried out in the same manner as in Example 10 except that cobalt naphthenate was used as a catalyst species and an amount for use of catalyst was 20 ppm as a solution concentration.

Data in a stationary state were analyzed. As a result, it was found that the selectivity to metaxylylene diisocyanate was 89.7% and the selectivity to monoisocyanate as an intermediate product was 3.2% in the MXDU decomposition percentage of 95.2%. The phenomena were observed that brown solid substances began to deposit from about 4 hours after operation starting and then adhered to the wall of the reactor, and gradually accumulated.

EXAMPLE 11

The experiment for thermal decomposition of 1-methyl-2,4-bis (ethoxycarbonylamino) benzene was carried out.

350 ml of a solution dissolved 50 ppm of metaxylene-4-sulfonic acid in Marotherm S solvent was charged into the reactor in the same manner as in Examples 9 and 10. The experiment was carried in the same conditions as in Examples 9 and 10 except that 1-methyl- 2,4-bis (ethoxycarbonylamino) benzene / Marotherm S was charged in a ratio of 1/1 by weight into a bath for raw material maintained at a constant temperature and then metaxylene-4-sulfonic acid was added thereto to prepare a solution having a metaxylene-4-sulfonic acid concentration of 50 ppm. Data in a stationary state were analyzed. As a result, it was found that the selectivity to tolylene-2,4-diisocyanate was 94.8% and the selectivity to monoisocyanate as an intermediate product was 2.8% in the 1-methyl-2, 4-bis (ethoxycarbonylamino) benzene decomposition percentage of 99.8%. The operation was continued for 12 hours. Neither adhesion nor sedimentation of solid substances was observed in both the reactor and the receiver.

In the process according to the present invention, a high thermal decomposition rate of carbamic acid esters can be provided and side reaction wherein high boiling point by-products are produced can be suppressed, and furthermore isocyanates can be produced in a high space-time yield, by using non-metallic sulfonic acids as a catalyst.

Moreover, since neither heavy metal nor heavy metal compound are used as a catalyst as in prior art, neither adhesion nor sedimentation of high boiling point products due to deterioration and deactivation of catalyst occurs and stationary operation can be carried out for a long term, and treatment of catalyst after use also is easy.

Thus, according to the process in the present invention, isocyanates can be industrially produced with very great advantages.

TABLE 1

| Example and Comp. Ex. | Species of catalyst | Amount for use (g) | Thermal decomposition rate ($h^{-1}$) |
|---|---|---|---|
| Comp. Ex. 1 | absence of catalyst | — | 0.145 |
| Example 1 | naphthalene-β-sulfonic acid | 0.15 | 1.91 |
| Example 2 | methanesulfonic acid | 0.15 | 1.38 |
| Example 3 | benzenesulfonic acid | 0.15 | 0.97 |
| Example 4 | paratoluenesulfonic acid | 0.15 | 1.09 |
| Example 5 | paratoluenesulfonic acid | 0.29 | 1.95 |
| Example 6 | metaxylene-4-sulfonic acid | 0.15 | 1.15 |
| Example 7 | potassium methanesulfonic acid | 0.15 | 0.90 |
| Example 8 | sodium metaxylene-4-sulfonic acid | 0.15 | 1.99 |

What is claimed is:

1. A process for producing an isocyanate from a carbamic acid ester which comprises thermally decomposing the carbamic acid ester at a temperature of 150° to 350° C. in the presence of a catalyst consisting of an organic sulfonic acid to form the isocyanate and an alcohol.

2. A process according to claim 1, wherein the organic sulfonic acid has the formula $R^1SO_3H$ where $R^1$ is an organic group selected from the group consisting of aliphatic groups, alicyclic groups, aromatic groups and aralkyl groups.

3. A process according to claim 2, wherein $R^1$ is a halogen-substituted, alkoxy-substituted or nitro-substituted organic group.

4. A process according to claim 1, wherein the isocyanate and the alcohol are separately recovered.

* * * * *